United States Patent [19]

Kuack

[11] Patent Number: 5,981,405
[45] Date of Patent: *Nov. 9, 1999

[54] MUGWORT-IMPREGNATED SHEET AND METHOD FOR MAKING THE SAME

[75] Inventor: ChangGun Kuack, 1129, Chegi 2-dong, Tongdaemun-gu, Seoul, Rep. of Korea

[73] Assignee: ChangGun Kuack, Seoul, Rep. of Korea

[ * ] Notice: This patent is subject to a terminal disclaimer.

[21] Appl. No.: 09/123,501

[22] Filed: Jul. 28, 1998

[30] Foreign Application Priority Data

Jul. 29, 1997 [KR] Rep. of Korea ........................ 97-35848
Feb. 20, 1998 [KR] Rep. of Korea ......................... 98-5326

[51] Int. Cl.⁶ .................................................... B32B 27/04
[52] U.S. Cl. ................................ 442/44; 442/58; 427/202
[58] Field of Search .................................. 442/43, 44, 58; 427/180, 202

[56] References Cited

U.S. PATENT DOCUMENTS 4,689,408  8/1987  Gelman et al. ............................ 536/98
5,741,400  4/1998  Kwak ........................................ 162/158

Primary Examiner—Christopher Raimund
Attorney, Agent, or Firm—Baker & McKenzie

[57] ABSTRACT

A method of making a mugwort-impregnated sheet is disclosed. The method employs an apparatus comprising a release drum having a roll of meshed linen wound thereon, a withdrawal drum for withdrawal the meshed linen from the release drum, a device for applying a binder on the meshed linen while the meshed linen is withdrawn to the withdrawal drum; and a device for applying a mugwort powder on the meshed linen while the meshed linen is withdrawn to the withdrawal drum.

3 Claims, 4 Drawing Sheets

MUGWORT-IMPREGNATED SHEET AND METHOD FOR MAKING THE SAME

BACKGROUND OF THE INVENTION

1. Field of the Invention

The present invention relates to a mugwort-impregnated sheet and a method for manufacturing the same and, more particularly, to a mugwort-impregnated sheet which is suitable for use in a hygienic band, and a method for making the same.

The present invention further relates to a system for making a mugwort-impregnated sheet.

2. Description of the Prior Art

The applicant has researched and developed a hygienic band using mugwort which has medicinal properties that are effective in stopping bleeding, the refining of blood, treating cuts and abrasions, alleviating pain and inflammation, and getting rid of bad odors. As a result, a method for manufacturing a mugwort-impregnated pad has been developed. This method is disclosed in U.S. Pat. No. 5,741,400.

In this patent, the hygienic band comprises a pad and a mugwort sheet attached on the pad. The mugwort sheet is made of a nap/pulp mixture. The mugwort naps are obtained through the steps of breaking a lump of dry mugwort and straining the crushed mugwort.

The nap/pulp mixture is dehydrated to be the mugwort sheet. That is, the disclosed mugwort sheet contains a natural pulp, reducing the amount of the mugwort material In addition, a plurality of apertures through which blood flows into the pad must be formed on the sheet through a perforation process, causing decreased productivity. Furthermore, the more than 70% of the sheet is wasted in forming the apertures. Although these chips to make the apertures are recycled, additional costs are involved in the recycling process.

SUMMARY OF THE INVENTION

Therefore, the present invention has been made in an effort to solve the above described problems of the prior art.

It is an object of the present invention to provide a mugwort-impregnated sheet which is suitable for use as a hygienic band and is inexpensively made through a simple process.

According to one aspect of the present invention, a mugwort-impregnated sheet comprises a paper made of pulp, and a dissociated mugwort naps added on at least one side of the paper.

According to another aspect of the present invention, a method for making mugwort-impregnated sheet, comprising the steps of crushing a lump of dry mugwort into 50–150 mesh size pieces, straining the crushed mugwort to obtain a certain amount of mugwort naps without stalk and chlorophyll, fumigating the mugwort naps in a steam boiler having a temperature of about 300° and pressurized to roughly 2–3ton/m$^3$, dissociating the mugwort naps in a first refiner; applying the mugwort naps on a draft paper which is made by dissociating a lump of pulp in a second refiner, to obtain a drafting mugwort sheet, dehydrating the drafting mugwort sheet.

According to still another aspect of the present invention, a mugwort-impregnated sheet comprising a meshed linen, a binder applied on the meshed linen in latitude and longitude pattern, and a mugwort powder applied on a surface of the meshed linen.

According to yet another aspect of the present invention a method for making a mugwort-impregnated sheet, comprising the steps of applying a binder on a meshed linen in latitude and longitude pattern, and applying a mugwort powder on the surface of the meshed linen.

The mugwort powder is applied on the pattern by a sprayer.

According to yet another aspect of the present invention, a system for making a mugwort-impregnated sheet comprising a release drum having a roll of meshed linen wound thereon, a withdrawal drum for withdrawal the meshed linen from the release drum, means for applying a binder on the meshed linen while the meshed linen is withdrawn to the withdrawal drum; and means for applying a mugwort powder on the meshed linen while the meshed linen is withdrawn to the withdrawal drum.

The means for applying a binder comprises a sprayer.

The means for applying a mugwort powder comprises a reservoir containing the mugwort powder.

The system further comprises a guider for guiding the meshed linen.

The meshed linen is selected from the group consisting of a gauze and a lace.

BRIEF DESCRIPTION OF THE DRAWINGS

A more complete appreciation of this invention, and many of the attendant advantages thereof, will be readily apparent as the same becomes better understood by reference to the following detailed description when considered in conjunction with the accompanying drawings in which like reference symbols indicate the same or similar components, wherein.

DETAILED DESCRIPTION OF PREFERRED EMBODIMENT

Figure 1:
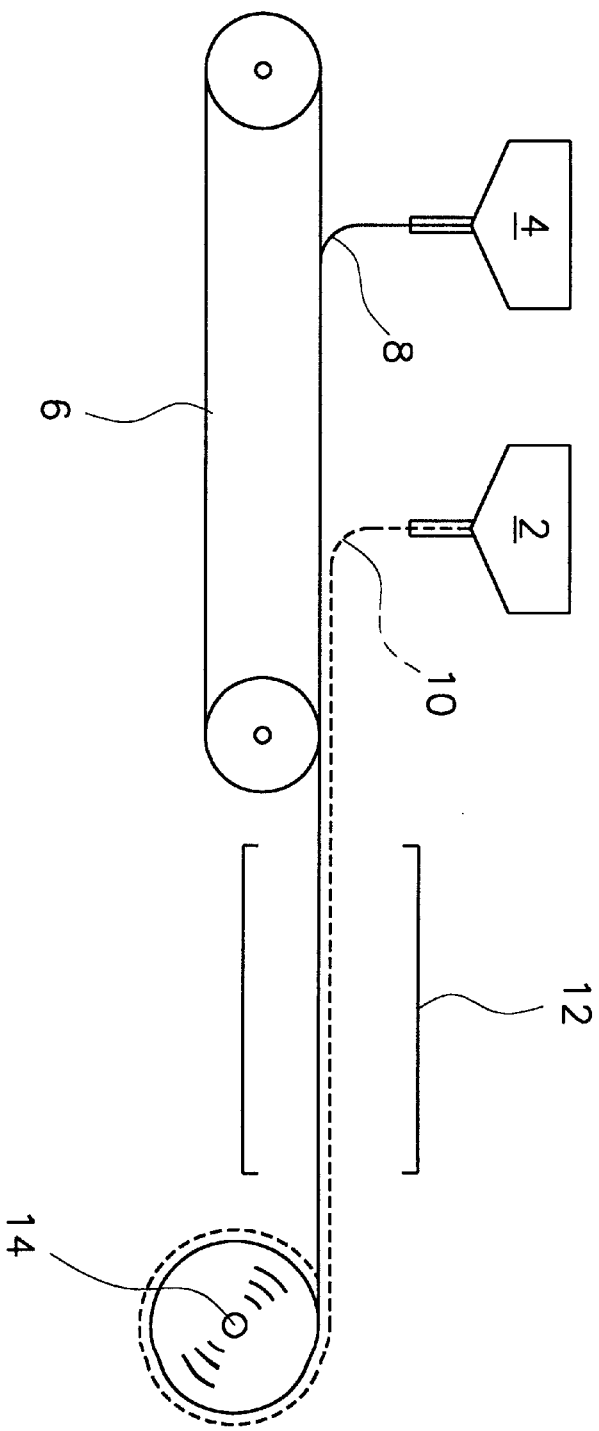
FIG. 1 is a schematic view showing a mugwort-impregnated sheet manufacturing process according to a first embodiment of the present invention.

Referring to FIG. 1, there is shown a schematic view illustrating a mugwort-impregnated sheet manufacturing process according to a first embodiment of the present invention;

First, a lump of dry mugwort is crushed into 10–150 mesh size pieces and is then strained through a sieve to obtain a certain amount of mugwort naps without stalk and chlorophyll. The mugwort naps are fumigated in a steam boiler having a temperature of about 300° C. and pressurized to roughly 2–3ton/m$^3$. After this, the mugwort naps are dissociated in a first refiner 2. At this point, a lump of pulp is separately dissociated in a second refiner 4.

The pulp dissociated in the second refiner 4 is transmitted to a drafting paper-making machine 6 to obtain drafting paper 8 having a predetermined thickness. The mugwort naps dissociated in the first refiner 2 is applied on or merged with the draft paper 8, thereby obtaining a drafting mugwort sheet 10.

The drafting mugwort sheet 10 is dehydrated and dried through a dry process and is then rolled around a winding roller 14, thereby obtaining a pad material.

The pad material is multi-layered to result in the mugwort impregnated hygienic band.

In the above first embodiment, the drafting mugwort sheet 10 can be applied on an entire surface of the drafting paper 8 or applied in a plurality of strands state on the surface of the drafting paper 8 in a predetermined pattern.

Figure 2:
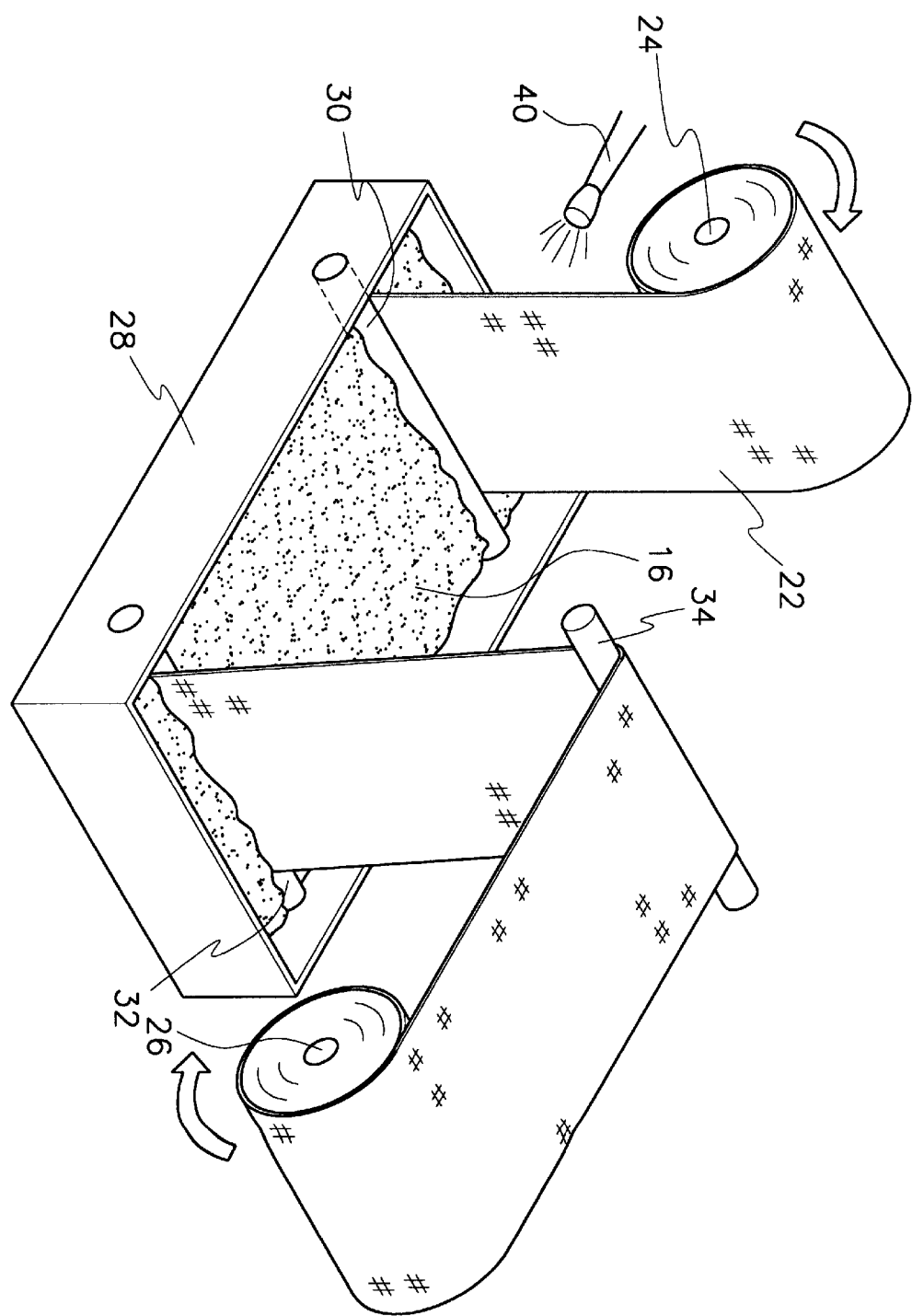
FIG. 2 is a schematic perspective view showing a mugwort-impregnated sheet manufacturing process according to a second embodiment of the present invention.
Figure 3:
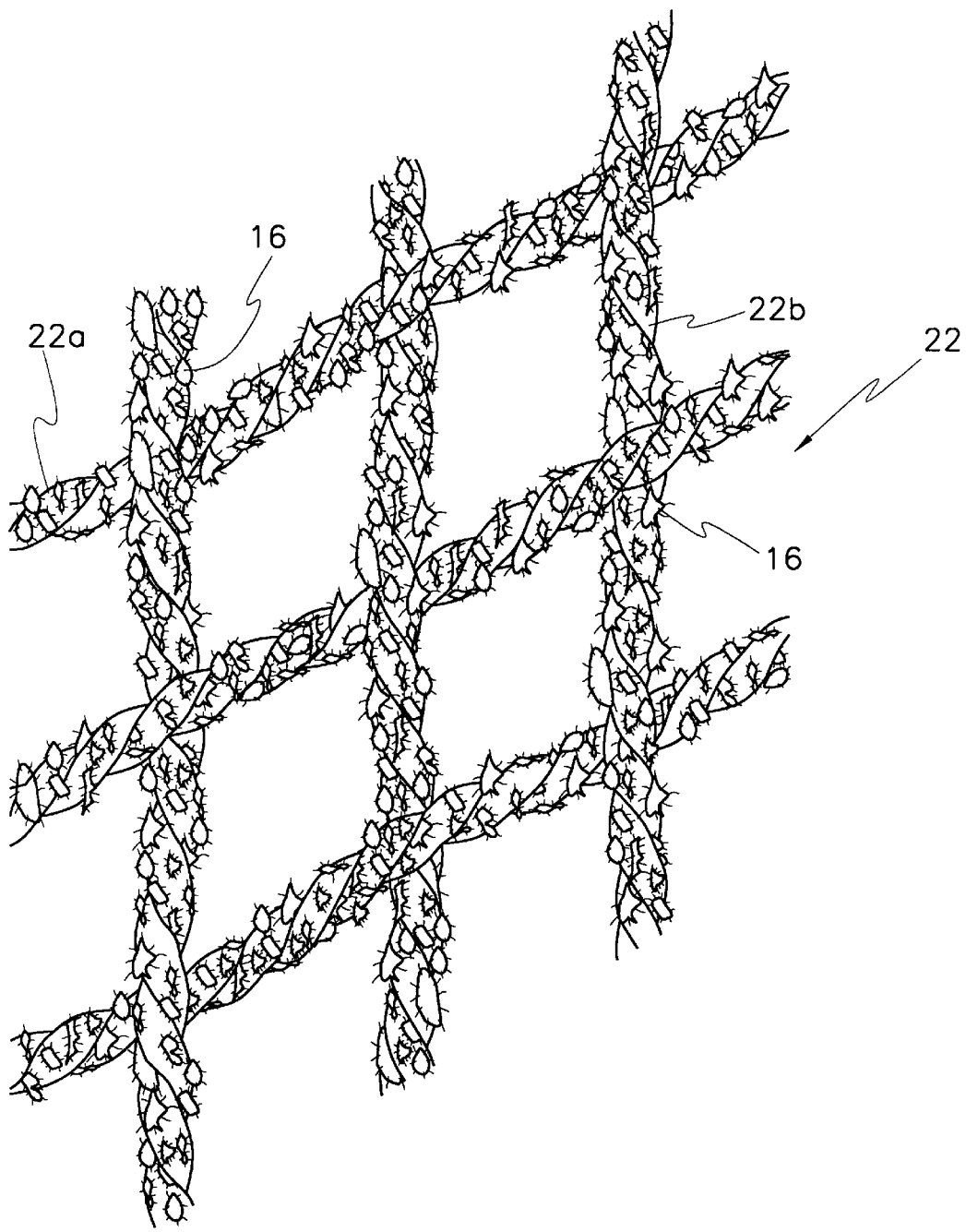
FIG. 3 is a partly enlarged perspective view showing a mugwort-impregnated sheet obtained through the process depicted in FIG. 2.

FIG. 2 shows a schematic perspective view showing a mugwort-impregnated sheet manufacturing process according to a second embodiment of the present invention.

In this embodiment, the mugwort-impregnated sheet is made by applying mugwort powder on a meshed linen 22 such as gauze or lace.

The meshed linen 22 passes through a reservoir 28 containing the mugwort powder while it is wound from a release drum 24 to a withdrawal drum 26. The release and withdrawal drum 24 and 26 are driven by a driving system (not shown) at a predetermined speed.

The meshed-linen 22 is guided by a pair of guide rollers 30 and 32 which are oppositely disposed within the reservoir 28. If necessary, an additional guide roller 34 may be disposed on a moving path of the meshed linen 22.

A binder is applied on the meshed-linen 22 before the meshed linen 22 goes into the reservoir 28. The binder is sprayed through a nozzle 40 disposed close to the release drum 24.

The most suitable material as the binder is carboxymethylcellulose since viscosity thereof can be easily adjusted by adjusting pH thereof. The mugwort power contained in the reservoir 28 is attached on the binder applied on the meshed linen 22 while it passes through the reservoir 28.

The mugwort power may be applied on only one surface or both surfaces of the meshed linen 22. Therefore, when the mugwort power is applied on both surfaces of the meshed linen 22, a pair of nozzles 40 are disposed toward the both surfaces of the meshed linen 22.

More preferably, the nozzles 40 are disposed to spray the binder while reciprocally moving along a width direction of the meshed linen 22.

The binder applying means is not limited to the nozzle 40. As an another embodiment, there may be provided a container containing the binder on the meshed linen moving path so that the meshed linen 22 can be immersed while moving along the path.

In this embodiment, when the carboxymethylcellulose is adjusted to be neutral pH or low alkaline, it appears the high viscosity good enough to bind the mugwort powder.

While the meshed linen 22 passes through the reservoir 28, the mugwort power 16 is attached on the surface of the meshed linen in the latitude and longitude directions.

The meshed linen 22 applied with the mugwort powder 16 is wound around the withdrawal drum 26, if required, after it is dried. It is preferable that the meshed linen 22 applied with the mugwort powder is dried by a forced dry method using dry air.

It is also considerable to vibrate the reservoir 28 so that the mugwort power 16 can be applied on the meshed linen 22 evenly.

Figure 4:
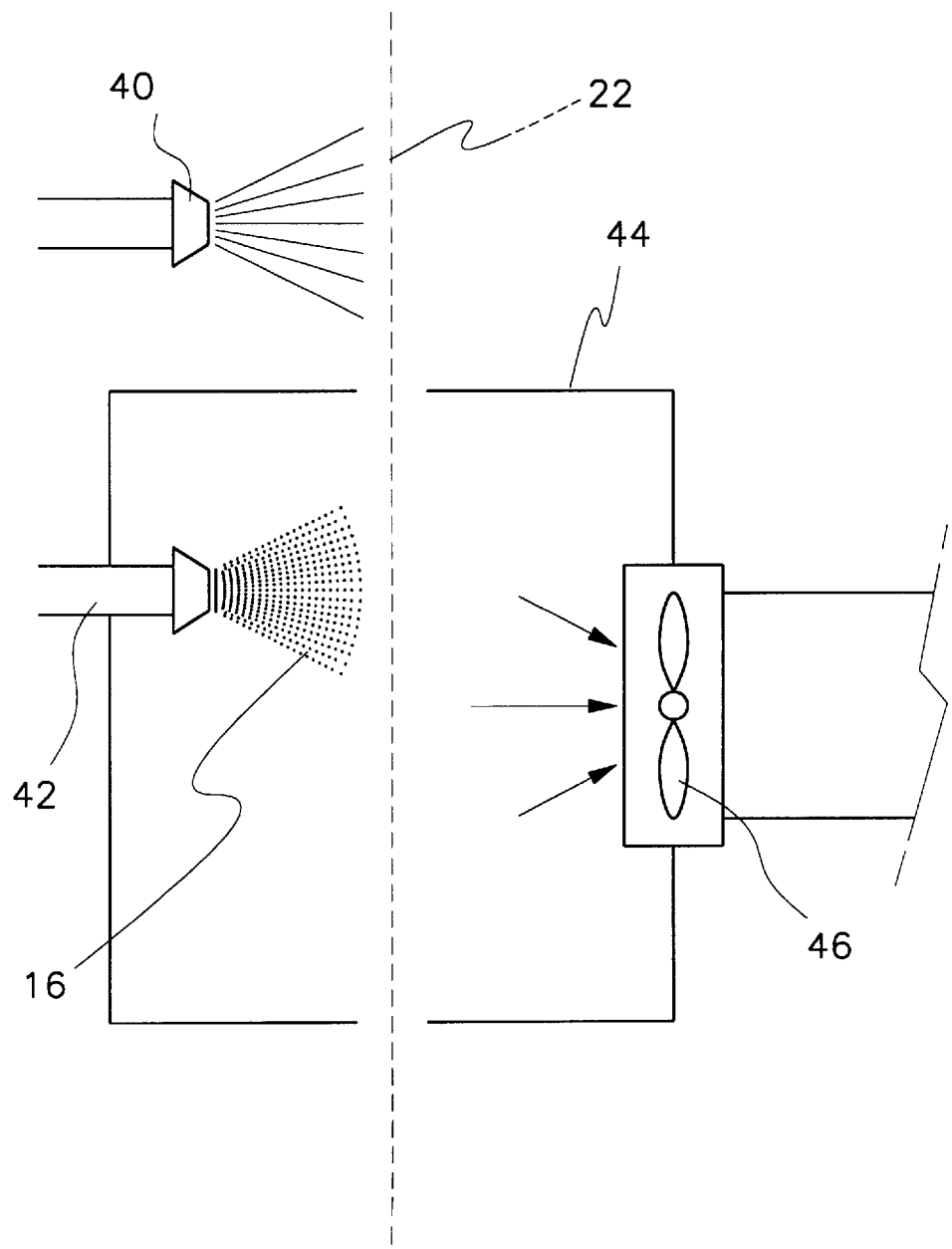
FIG. 4 is a schematic side view showing a modified example of the second embodiment.

Alternatively, the mugwort power 16 may be applied on the meshed linen 22 by being sprayed through a nozzle 42 as shown in FIG. 4. At this point, a partition wall 44 is disposed around the nozzle 42 to provide a shielded area where the mugwort power wafts. The wafting mugwort 16 is returned to the nozzle 42 through a fan 46 disposed beside the partition wall 44.

The above described meshed linen 22 obtained through the above described method is cut in a predetermined size and insert into a pad for a hygienic band.

In this embodiment, since the mugwort paper is made of a meshed linen, an aperture forming process is not required, making the process simple and the manufacturing costs be saved.

What is claimed is:

1. A mugwort-impregnated sheet comprising:

a meshed linen;

a binder applied on the meshed linen in a latitude and longitude pattern; and a mugwort powder applied on the meshed linen.

2. A method for making a mugwort-impregnated sheet, comprising the steps of:

applying a binder on a meshed linen in latitude and longitude pattern; and applying a mugwort powder on the meshed linen.

3. The method of claim 2 wherein the mugwort powder is applied on the meshed linen by a sprayer.

* * * * *